(12) United States Patent
Hempel

(10) Patent No.: US 7,648,498 B2
(45) Date of Patent: Jan. 19, 2010

(54) IRRADIATION DEVICE FOR INFLUENCING A BIOLOGICAL STRUCTURE IN A SUBJECT WITH ELECTROMAGNETIC RADIATION

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 522 days.

(21) Appl. No.: 11/358,806

(22) Filed: Feb. 21, 2006

(65) Prior Publication Data

US 2006/0206108 A1 Sep. 14, 2006

(30) Foreign Application Priority Data

Feb. 21, 2005 (DE) .................... 10 2005 007 851

(51) Int. Cl.
*A61B 18/04* (2006.01)
(52) U.S. Cl. .................... 606/33; 606/32; 607/156
(58) Field of Classification Search .............. 606/1, 606/32, 33; 128/920; 607/100–102, 154–156; 600/10, 13, 14; 315/3.6, 3.5, 5, 111.41, 119, 315/39.59, 4, 5.41; 333/219.1, 1.1, 187, 333/135, 202, 219, 224, 231, 239; 343/742, 343/909, 700 MS, 726, 729, 752, 769; 331/107 A, 331/66, 83, 96; 324/658, 636
See application file for complete search history.

(56) References Cited

U.S. PATENT DOCUMENTS

| | | | | |
|---|---|---|---|---|
| 3,890,953 A | * | 6/1975 | Kraus et al. ................... 600/14 |
| 4,095,588 A | * | 6/1978 | Goldman et al. .............. 600/13 |
| 4,428,366 A | * | 1/1984 | Findl et al. .................... 600/14 |
| 4,458,689 A | * | 7/1984 | Sorenson et al. ............. 600/447 |
| 4,556,057 A | * | 12/1985 | Hiruma et al. .............. 600/476 |
| 4,583,556 A | * | 4/1986 | Hines et al. ................. 607/116 |
| 4,672,980 A | * | 6/1987 | Turner ........................ 607/154 |
| 4,712,042 A | * | 12/1987 | Hamm ....................... 315/5.41 |
| 4,829,252 A | * | 5/1989 | Kaufman .................... 324/309 |
| 4,884,886 A | * | 12/1989 | Salzman et al. ............. 356/367 |
| 4,932,951 A | * | 6/1990 | Liboff et al. .................. 600/13 |

(Continued)

FOREIGN PATENT DOCUMENTS

CN 1169321 A 7/1998

(Continued)

*Primary Examiner*—Linda C Dvorak
*Assistant Examiner*—Amanda Scott
(74) *Attorney, Agent, or Firm*—Schiff Hardin LLP

(57) ABSTRACT

An irradiation device for irradiating a living organism with electromagnetic radiation in order to influence biological structures inside the organism has a frequency generator that has a frequency synthesizer for the production of electromagnetic radiation having a defined frequency pattern, and a transmission antenna that is fashioned such that during operation the electromagnetic radiation is emitted essentially into a particular radiation volume. In addition, the irradiation device has an interface for acquiring structure-specific data for identifying a biological target structure that is to be influenced, a frequency pattern storage unit in which defined resonant frequency patterns allocated to various biological structures are stored, a frequency pattern selection unit for selecting a resonant frequency pattern from the frequency pattern storage unit on the basis of the acquired structure-specific data, and a control unit for controlling the RF generator in such a way that a subject to be irradiated, situated in the radiation space, is exposed to electromagnetic radiation having the selected resonant frequency pattern at a particular intensity and for a particular duration of irradiation.

15 Claims, 5 Drawing Sheets

U.S. PATENT DOCUMENTS

| | | | | |
|---|---|---|---|---|
| 4,974,503 | A * | 12/1990 | Koch | 99/451 |
| 5,045,050 | A * | 9/1991 | Liboff et al. | 600/9 |
| 5,067,940 | A * | 11/1991 | Liboff et al. | 600/13 |
| 5,087,336 | A * | 2/1992 | Liboff et al. | 600/14 |
| 5,100,373 | A * | 3/1992 | Liboff et al. | 600/13 |
| 5,160,591 | A * | 11/1992 | Liboff et al. | 204/155 |
| 5,163,446 | A * | 11/1992 | Saitoh | 607/101 |
| 5,183,456 | A * | 2/1993 | Liboff et al. | 600/9 |
| 5,207,223 | A * | 5/1993 | Adler | 600/427 |
| 5,217,003 | A * | 6/1993 | Wilk | 600/109 |
| 5,224,492 | A * | 7/1993 | Takahashi et al. | 607/154 |
| 5,224,922 | A * | 7/1993 | Kurtz | 600/13 |
| 5,284,144 | A * | 2/1994 | Delannoy et al. | 600/412 |
| 5,305,748 | A * | 4/1994 | Wilk | 600/407 |
| 5,317,265 | A * | 5/1994 | Weinstock et al. | 324/312 |
| 5,357,958 | A * | 10/1994 | Kaufman | 600/410 |
| 5,364,392 | A * | 11/1994 | Warner et al. | 606/34 |
| 5,368,031 | A * | 11/1994 | Cline et al. | 600/411 |
| 5,482,041 | A * | 1/1996 | Wilk et al. | 600/430 |
| 5,517,119 | A * | 5/1996 | Weinstock et al. | 324/312 |
| 5,540,681 | A * | 7/1996 | Strul et al. | 606/34 |
| 5,683,437 | A * | 11/1997 | Doty | 607/91 |
| 5,891,182 | A * | 4/1999 | Fleming | 607/50 |
| 5,899,857 | A * | 5/1999 | Wilk | 600/407 |
| 5,922,013 | A * | 7/1999 | Fallik | 607/101 |
| 6,048,301 | A * | 4/2000 | Sabuda | 600/9 |
| 6,100,683 | A * | 8/2000 | Lim et al. | 324/212 |
| 6,132,357 | A * | 10/2000 | Sabuda | 600/1 |
| 6,139,568 | A * | 10/2000 | Doty | 607/91 |
| 6,316,776 | B1 * | 11/2001 | Hiramoto et al. | 250/492.3 |
| 6,320,508 | B1 * | 11/2001 | Giesler et al. | 340/572.7 |
| 6,580,935 | B1 * | 6/2003 | Wach et al. | 600/310 |
| 6,933,819 | B1 * | 8/2005 | Koonce | 335/296 |
| 7,122,978 | B2 * | 10/2006 | Nakanishi et al. | 315/500 |
| 7,146,210 | B2 * | 12/2006 | Palti | 607/2 |
| 7,415,301 | B2 * | 8/2008 | Hareyama et al. | 600/427 |
| 2004/0069776 | A1 * | 4/2004 | Fagrell et al. | 219/690 |
| 2005/0231138 | A1 * | 10/2005 | Nakanishi et al. | 315/500 |
| 2008/0153424 | A1 * | 6/2008 | Laroche | 455/67.16 |

FOREIGN PATENT DOCUMENTS

| | | | |
|---|---|---|---|
| DE | 3207708 | A1 * | 9/1983 |
| DE | 3508674 | A1 * | 9/1986 |
| EP | 196180 | A2 * | 10/1986 |
| EP | 279779 | A1 * | 8/1988 |
| EP | 293080 | A2 * | 11/1988 |
| EP | 333683 | A1 * | 9/1989 |
| EP | 0 928157 | B1 | 6/2004 |
| JP | 57211539 | A * | 12/1982 |
| JP | 01209073 | A * | 8/1989 |
| RU | 2 007 460 | C1 | 2/1994 |
| RU | 2 095 797 | C1 | 11/1997 |
| WO | WO 8803823 | A1 * | 6/1988 |
| WO | WO 00/15097 | | 3/2000 |

* cited by examiner

IRRADIATION DEVICE FOR INFLUENCING A BIOLOGICAL STRUCTURE IN A SUBJECT WITH ELECTROMAGNETIC RADIATION

BACKGROUND OF THE INVENTION

1. Field of the Invention

The present invention relates to an irradiation device for irradiating a living organism with electromagnetic radiation in order to influence biological structures inside the organism. In addition, the present invention relates to a control device for such an irradiation device.

2. Description of the Prior Art

Shortly after the discovery of electromagnetic waves by H. Hertz at the end of the 19th century, attempts began to be made to find therapeutic uses for radio-frequency or high-frequency electromagnetic fields and the heat induction they can produce. A relatively new technology is known as electromagnetic tomography or microwave tomography, which is regarded as having enormous potential in the field of medicine. This technology is explained, for example, in EP 0 928 157 B1. There, a spectroscopic method is described in detail that enables rapid, non-invasive imaging of various physiological tissue states, using multi-frequency radiation. For this, microwaves are used in the range from 0.5 to approximately 3 GHz. This document also proposes the use of microwaves for the ablation of diseased tissue. Here, using radiation with microwaves as an alternative to the use of a laser, the temperature in the area of tissue to be removed is increased high enough so that the tissue is removed. For this purpose, electromagnetic waves are used that are not selective for a specific biological structure, so that more than only the tissue to be removed is influenced, insofar as the action of the electromagnetic energy is not geometrically limited to a particular target area. For this reason, it is necessary to focus the electromagnetic energy as precisely as possible on the tissue that is to be removed, in order not to destroy the surrounding tissue.

One possibility for the well-directed influencing of only a particular biological target structure, while leaving other nearby biological structures almost uninfluenced, is the use of radiation having a particular frequency, or a particular frequency pattern, that triggers resonance effects in the biological target structure.

Thus, in principle it is known that every system has an acoustic resonant frequency that corresponds to the natural free oscillation frequency of the system. The term "resonance catastrophe" refers to a system capable of oscillation being excited from the outside with its resonant frequency, also called the eigenfrequency. As the excitation continues with sufficient strength, the summed oscillation forces can become large enough so that the system or the material thereof is destroyed. Consequently, the system can be excited by small mechanical or acoustic oscillating forces in a very narrow frequency band close to or equal to the resonant frequency, inducing a resonance in the target structure that has a strong influence on the target structure, leading to its destruction. The same is true for electromagnetic resonant circuits, in which, due to radiation or the application of current or power in the range of the resonant frequency of the resonant circuit, the impedance goes to zero, so that in the theoretically ideal case an infinitely large current peak or surge is produced even with low input energy.

A method for the selective detection, identification, and/or influencing of biological structures using acoustic and/or acousto-electromagnetic resonance is described in detail in WO 00/15097. In this document, it is also specified that the energy in a structure that is in a state of resonance increases very quickly, and this energy either remains in the structure or is emitted back to the environment in the form of acoustic and/or electromagnetic energy. The energy remaining in the structure can influence the functioning of the structure, and can even result in the destruction of the structure. If resonant acoustic energy in lower energy ranges that do not result in the destruction of the structure is radiated into the biological structure, the acoustic energy is converted into electromagnetic energy having particular field and frequency characteristics. The field and frequency characteristics of the emitted electromagnetic energy depend, inter alia, on the atomic or molecular composition of the structure, and are therefore indicative of the structure in question. This electromagnetic signal, which is emitted by a particular biological structure excited by resonant acoustic energy, and which has a definite frequency pattern, is therefore also called the "acousto-electromagnetic signature" of the structure. In the following, the term "frequency pattern" refers not only to the spectral position of the individual frequencies of the electromagnetic radiation, but also the intensity relationships of the various frequencies to one another. In the extreme case, however, a frequency pattern can be only a single frequency. Here, the term "frequencies" is to be understood as referring to frequency lines having a very narrow bandwidth.

It is conversely possible, by supplying electromagnetic energy into a biological structure with a resonant frequency pattern that corresponds to the acousto-electromagnetic signature of this structure, to set the structure into acoustic resonance. The resonant frequency of a structure depends on the shape, the size, and the composition of the structure. For example, a homogenous sphere has a resonant frequency having the wavelength of the diameter of the sphere. In WO 00/15097, the approximate acoustic resonant frequencies (given a speed of sound of 1500 m/s) are indicated for a series of biological structures. For example, the resonant frequency for plant cells is in the area of 15 MHz, for animal cells in the area of 150 MHz, for bacteria in the area of 1.5 GHz, for viruses in the area of 15 GHz, and for proteins in the area of 150 GHz.

In addition, WO 00/15097 also specifies that biological structures can be purposefully influenced in a wide variety of ways by radiating the acoustic resonant frequency and/or by radiating electromagnetic energy corresponding to the acousto-electromagnetic signature. For example, it is proposed to excite bone growth through the radiation of matched electromagnetic energy in order to help osteoporosis patients, or for example to help compensate the reduction of bone density in persons spending long periods of time outside the earth's gravitational field, e.g. in space stations. In particular, for this purpose the use of a sleeping bag is proposed in which an electromagnetic radiating element is situated that emits the acousto-electromagnetic signature of the bone structure, required in order to stimulate the bone growth, at low intensity.

In addition, it is proposed to destroy viruses by emitting acoustic energy in the matched resonance range. Thus, for the treatment of, for example, patients infected with HIV, an extracorporeal blood circulation system is proposed in which the blood is purposefully directed through a radiation zone in which the acoustic energy required for resonance excitation in the viruses is supplied. In a second exemplary embodiment, an intravascular system is proposed in which the required acoustic energy is applied directly inside the patient via nanofilters or suitably constructed catheters.

SUMMARY OF THE INVENTION

An object of the present invention is to provide a universally applicable and easily operated irradiation device of the type described above with which a wide variety of biological structures within a living organism can easily be influenced in a targeted manner, and with which, in particular, viruses, bacteria, fungi, carcinogenic cells, or other pathological sites can be destroyed without significantly damaging other biological structures inside the organism.

This object is achieved by an irradiation device according to the invention having a frequency generator that has a frequency synthesizer for producing electromagnetic radiation having a defined frequency pattern. The frequency pattern can be arbitrarily selected. For example, it can be a single frequency line, but it can also be a number of different frequencies having defined amplitudes relative to one another.

In addition, a transmission antenna is used that is fashioned such that during operation the electromagnetic radiation is emitted essentially only in a particular radiation volume. Here, the radiation volume is the volume in which the produced electromagnetic field has the desired, set strength in as homogenous a fashion as possible. The subject to be irradiated, i.e. the living organism in which the biological structures that are to be influenced by the radiation are located, is situated in the radiation volume.

Moreover, an interface is required for the acquisition of structure-specific data, such as for example a name, a type, an identifier, or the like, for the identification of a biological target structure that is to be influenced. This can be a user interface with which an operator of the irradiation device manually inputs the structure-specific data. Alternatively or in addition, however, it can also be an interface to other functional units in which appropriate data have already been stored, such as, for example, an interface to a radiological information system (RIS). Likewise, it can be a reading device for reading from data carriers on which the desired information is stored.

In addition, the irradiation device according to the present invention has a frequency pattern storage unit in which defined resonant frequency patterns allocated to various biological structures are stored, e.g. in a database, as well as a frequency pattern selection unit for selecting an associated resonant frequency pattern from the frequency pattern storage unit on the basis of the acquired structure-specific data of a biological target structure. Such a "resonant frequency pattern" of a biological structure is a frequency pattern of electromagnetic radiation that is suitable for the targeted setting of the relevant biological structure into a state of resonance, and thus for achieving the desired influencing of the biological structure without influencing other biological structures having different resonant frequency patterns.

The irradiation device according to the present invention has a control unit for controlling the RF generator so that a radiation subject situated in the radiation volume is exposed to electromagnetic radiation having the selected resonant frequency pattern with a particular intensity and for a particular duration of radiation. This control unit automatically determines the required control parameters, e.g. on the basis of the acquired structure-specific data and the selected frequency pattern, and gives these to the RF generator so that it will emit the suitable signals to the transmission antenna.

Using the irradiation device according to the present invention, it is easy to influence a wide variety of biological structures inside the organism in a predetermined manner. For this purpose, it is necessary merely to position the radiation subject in the radiation volume, and for the operator of the irradiation device to know the structure-specific data in order to identify the biological target structure that is to be influenced, for example a name or an identifier of a virus or of a bacterium. The operator then need merely input or select the structure-specific data of the biological target structure that is to be influenced. Subsequently, defined resonant frequency patterns associated with the target structure can automatically be selected, and the radiation subject is irradiated in a suitable manner with electromagnetic radiation having the relevant resonant frequency pattern.

Preferably, the device also has an interface for acquiring data that are specific to the radiation subject and/or data that are specific to the treatment. The data specific to the radiation subject can be, for example, the age, height, or weight of a patient, and/or (for example in the treatment of a viral disease) can be values representing a measure of the extent of the pathological condition in the body, such as a virus count. The treatment-specific data can for example be a therapeutic goal; e.g., whether the biological structures, such as viruses (in the case of a viral disease), are to be completely destroyed, or whether for example other biological structures, such as bone cells, are to be stimulated to growth. This interface can be a separate interface, for example an interface to a computer network such as an RIS, or a data carrier reading device. The interface also can be the interface already used for the acquisition of the structure-specific data, e.g. the user interface.

In this exemplary embodiment, the control unit is configured to select, on the basis of the data specific to the radiation subject and/or the treatment-specific data, the intensity and the duration of radiation, and the RF generator is correspondingly controlled so that the radiation subject situated in the radiation volume is exposed to a particular therapeutic dose of the desired electromagnetic radiation.

Preferably, the device has a positioning mechanism for positioning the radiation subject inside the radiation volume. This can be a simple platform or can be a platform that can be adjusted, or the like.

Preferably, the radiation volume is fashioned and dimensioned such that an adult person who is to be irradiated can be contained completely inside the radiation volume. That is, the transmission antenna is fashioned such that the entire body of this person can be irradiated with the desired electromagnetic radiation. In contrast to the method described in WO 00/15097, in which the blood of an HIV-infected patient is purposefully conducted through a radiation zone, this has the advantage that the viruses not situated in the blood of the patient can also be destroyed, so that not merely a reduction of the viruses, but an almost complete destruction of all the viruses, is achieved.

In order to enable the desired frequencies to be transmitted in as narrowband a fashion as possible, the transmission antenna can be fashioned as a resonant circuit, or can form a part of such a resonant circuit. By the suitable setting of the components of this resonant circuit, it can be ensured that the transmission antenna will transmit, in a well-directed fashion, very sharp frequencies corresponding to the selected frequency pattern. That is, the radiation subject can then be irradiated for example with the maximum oscillation amplitude at a precisely defined frequency—the resonant frequency of the resonant circuit.

In order to achieve as homogenous a field propagation as possible in the radiation volume, a transmission antenna is preferably used that embodies a solenoid coil and/or a Helmholtz coil or a saddle coil that surrounds the radiation volume.

Such coils are distinguished by having a particularly homogenous field in the interior of the coil. In order to enable the irradiation of relatively large radiation subjects, for example an entire human body, with a high degree of field homogeneity, it is quite preferred to use a transmission antenna having a birdcage antenna structure, as is also used, for example, as a transmission antenna in magnetic resonance tomography.

In order to optimize the signal-to-noise ratio, independent of the type of antenna used care should be taken to achieve as high a filling factor as possible. The dimensions of the antenna therefore should be selected such that the internal space of the antenna, serving as the radiation volume, is adapted to the dimensions of the radiation subject, and surrounds the radiation subject as closely as possible. That is, the radiation volume should not, as far as possible, be much larger than the subject to be irradiated should.

The transmission antenna is preferably integrated in a housing that encloses the radiation volume. In particular given the use of a solenoid coil, a saddle coil, or a birdcage antenna, the housing is fashioned in the shape of a tube, and the radiation volume is situated inside the tube.

If the device according to the present invention is to be used to implant a whole-body irradiation of a patient, this patient must be situated completely inside the radiation volume. If the transmission antenna, and consequently the housing enclosing the radiation volume, is designed such that the filling factor is as large as possible, this housing must enclose the patient relatively narrowly. Day-to-day practice in magnetic resonance tomography has shown, however, that most people find it extremely unpleasant to be enclosed in a narrow confinement for a long period of time. In persons having tendencies to claustrophobia, this can result in extreme states of panic, so that the treatment cannot be carried out at all. It is therefore advantageous for the housing to be fashioned so as to be at least partially transparent.

Preferably, the housing is divided by a plane running in a longitudinal direction of the housing, and has a housing base and a housing cover that can be opened and closed. Preferably, this housing is fashioned so as to be able to be folded open and shut around a pivot axis that runs in a longitudinal direction of the housing. This additional construction has the advantage that the person to be irradiated can lie down on a platform inside the housing while the housing is open, as for example in a tanning bed, and can then close the housing by folding it shut, rather than being moved longitudinally into the tube-shaped housing (as is conventional, for example, in magnetic resonance scanners and computed tomography scanners), which is also experienced as unpleasant by the patient.

In the frequency pattern storage unit, resonant frequency patterns can be stored for a wide variety of viruses and/or bacteria. Such a device then can be used arbitrarily for treating a wide variety of viral diseases and bacterial diseases in order to destroy the relevant viruses and bacteria in a targeted fashion without negatively influencing the organism of the person being treated. The stored resonant frequency patterns preferably are the acousto-electromagnetic signature of the relevant biological structures, i.e., for example of the viruses and/or bacteria.

Because new viruses and bacteria are constantly coming into existence and being identified, having correspondingly modified resonant frequency patterns, the device preferably also has a measurement device for determining the resonant frequency pattern of an (isolated) biological structure. Such a measurement device can have, for example, a noise generator for emitting electromagnetic white noise in a particular frequency range into a sample including the relevant isolated biological structure, a detector for acquiring the electromagnetic radiation emitted by the sample in reaction to the white noise, and an analysis device for determining the resonant frequency pattern on the basis of the electromagnetic radiation received by the detector. Preferably, this measurement device is connected to the frequency pattern storage unit in order to store the resonant frequency pattern determined for a particular biological structure in the frequency pattern storage unit, while assigning the structure-specific data for the identification of the relevant biological structure.

Consequently, in this method a resonant frequency pattern is determined by the reaction to non-specific electromagnetic radiation that is sent out uniformly in a broad frequency range. Alternatively, the acousto-electromagnetic signature can be determined as a resonant frequency pattern by radiating resonant acoustic energy, for example using piezoelectric transmitters, and acquiring and evaluating the electromagnetic response sent out by the sample, as is described in WO 00/15097. In this case, the measurement device has, instead of the noise generator, an appropriate device for sending the sound waves into the sample having the relevant structure.

Alternatively or in addition to such a measurement device for determining the resonant frequency pattern of a biological structure, the irradiation device can have an interface for receiving resonant frequency patterns, preferably with the associated structure-specific data for the identification of the relevant biological structures that were already determined by other devices. This interface can be a separate interface, or can be the interface already mentioned above for receiving the structure-specific, treatment-specific, and/or examination subject-specific data. This interface can also be a data carrier reading device.

Upon the appearance of a new virus (e.g., when there is the threat of a flu epidemic), it is then possible, for example at a central device, to identify the virus and isolate it, and subsequently to use the cited method to determine a resonant frequency pattern (and, if necessary, also additional information such as the required intensity and time duration, possibly dependent on particular patient data such as height, age, weight, etc.) in order to destroy the viruses in the body by irradiating a person. This data set can then be communicated to all irradiation devices according to the present invention that are provided with a corresponding interface and are suitably equipped, irradiation devices for example in various clinics or in physicians' practices. Before the treatment, the on-location personnel then need merely enter the patient-specific data, such as for example height, age, weight, and the structure-specific data, for example the precise type of virus, so that the irradiation device then automatically provides the correct setting in order to treat the patient infected with the relevant flu virus and to largely destroy the viruses. Depending on the intensity of the disease, i.e., the quantity of viruses present, this can take place in one session or in a number of sessions.

Due to the fact that the irradiation device is networked, via the aforementioned interface, with other irradiation devices and/or with a resonant frequency pattern measurement device, the various irradiation devices can consequently be regularly updated, so that a well-directed, large-coverage treatment of infected groups of persons is possible, without great expense, in order to achieve an early containment of epidemics.

Another component of the present invention is a control device for an RF irradiation device of the type described above. Such a control device has a control parameter output for connecting the RF generator, as well as a data input for acquiring structure-specific data for identifying a biological structure that is to be influenced. In addition, the control device has a frequency pattern storage unit in which defined resonant frequency patterns allocated to various biological structures are stored, and a frequency pattern selection unit in order to select a resonant frequency pattern from the frequency pattern storage unit on the basis of the acquired structure-specific data. In addition, this control device has a control unit in order to send control parameters to the RF generator via the control parameter output, so that the RF generator produces, for a determined time period, a signal having the selected frequency pattern and having a particular intensity.

DESCRIPTION OF THE PREFERRED EMBODIMENTS

Figure 1:
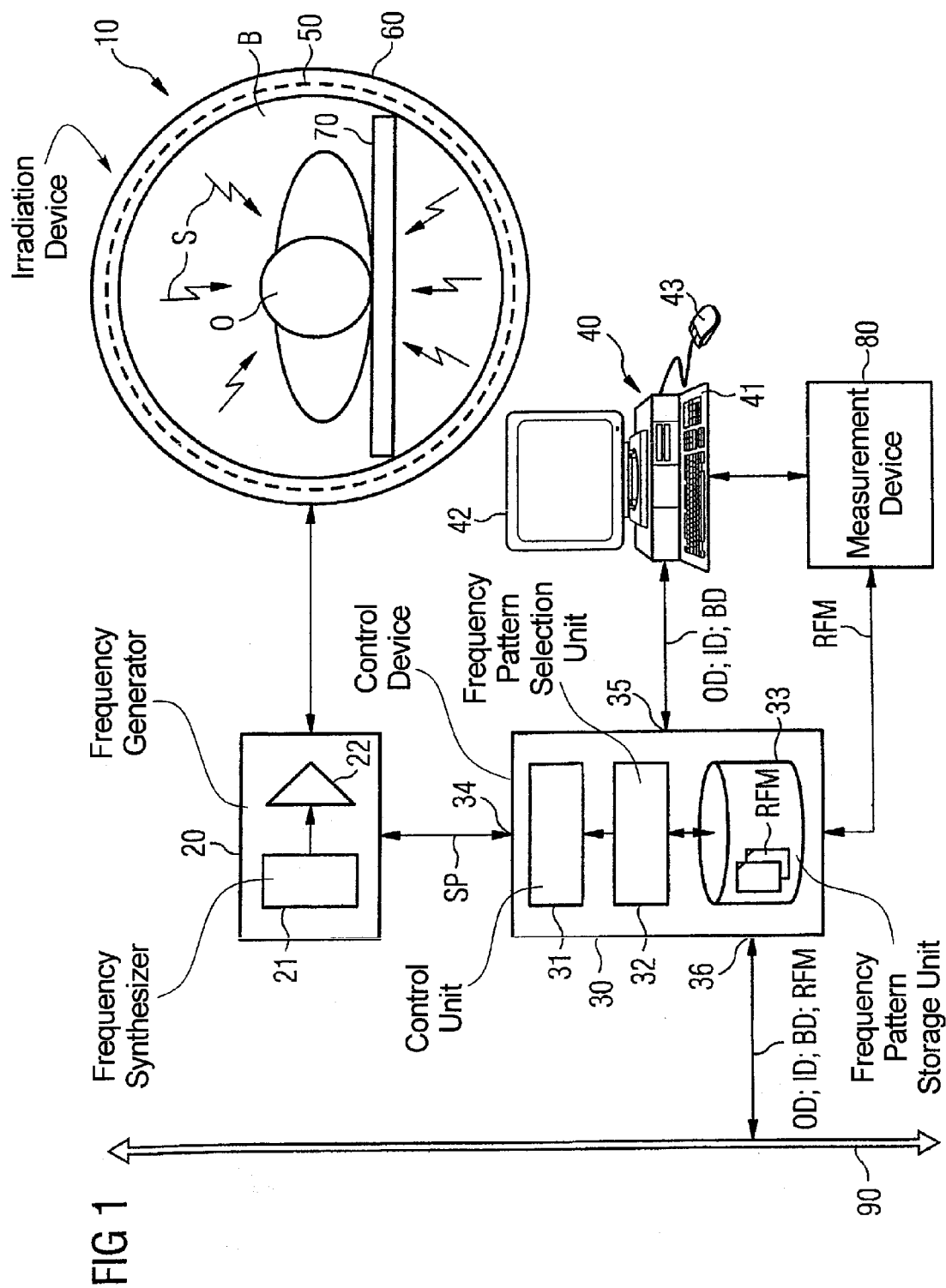
FIG. 1 shows a schematically illustrates an exemplary embodiment of an irradiation device according to the present invention.

The irradiation device 10 shown in FIG. 1 can be used for the whole-body irradiation of a person. For this purpose, irradiation device 10 has a transmission antenna 50 having a cylindrical structure—in this case, a birdcage antenna 50. The transmission antenna 50 is situated in a tube-shaped housing 60 having a cylindrical interior radiation space B, in which the radiation subject O, i.e., the person to be irradiated, is positioned on a platform. The precise design of housing 60 and the transmission antenna 50 is explained in more detail below.

In order for the transmission antenna 50 to emit the radio-frequency electromagnetic radiation S into radiation subject O, this antenna is connected to a frequency generator 20. This is an RF generator 20 which is preferably able to generate RF signals from the kilohertz range into the gigahertz range. A component of this frequency generator 20 is a frequency synthesizer 21 which is capable of producing an electrical alternating voltage signal having a very narrowband frequency, which signal is then amplified by amplifier 22 and supplied to antenna 50. In particular, frequency synthesizer 21 is fashioned such that a frequency pattern can be produced that is composed of a number of narrowband frequencies having defined amplitude relations. For this purpose, frequency generator 20 can have a number of frequency synthesizers 21 that, for example, operate in different frequency ranges, and/or subsequently connected amplifiers 22 that can be operated as desired, or simultaneously, depending on the desired output frequency pattern that is to be conducted to the antenna.

The frequency synthesizer is controlled by a control device 30. The basic components of this control device are a frequency pattern storage unit 33, a frequency pattern selection unit 32, and a control unit 31.

In the frequency pattern storage unit 33, the resonant frequency patterns RFM for each of various biological structures are stored in a database, for example various types of viruses, types of bacteria, and fungi. The resonant frequency patterns RFM are for example the acousto-electromagnetic signatures of the relevant biological structures. The allocation of the individual resonant frequency pattern RFM containing the data concerning the individual frequencies and relative amplitudes of the respective frequencies takes place with the aid of structure-specific data, such as e.g. the name of the structure, a type indication, an identifying number, etc.

A user interface 40, for example a PC having a display screen 42, a keyboard 41, and a mouse 43, is connected to a first data input 35 of control device 30. Via this user interface 40, an operator can for example input the structure-specific data ID, and communicate them to control device 30. On the basis of the entered structure-specific data ID, e.g. on the basis of the name or the identifier of a particular virus, the frequency pattern selection device 32 then searches for an associated resonant frequency pattern RFM in frequency pattern storage unit 33, and communicates it to the control unit 31.

Moreover, via the user interface 40 the operator can also communicate radiation subject-specific data OD, such as for example the age, height, weight, and sex of the person to be irradiated, to control device 30. It is likewise possible for the operator to input additional particular treatment-specific data BD, such as a therapeutic goal, e.g. the destruction of all viruses of the inputted type, and to communicate this to control device 30. On the basis of all these data and the selected resonant frequency pattern RFM, control device 31 then determines suitable control parameters SP. These control parameters SP are then emitted, at a parameter output 34, to frequency generator 20, so that this frequency generator emits a signal to the transmission antenna 54 precisely for a defined period of time, i.e., the irradiation duration, and with a particular intensity, so that this signal correspondingly radiates electromagnetic radiation S having the desired resonant frequency pattern RFM into radiation space B, and thus onto the person O to be irradiated.

Via the user interface 40, the operator also can monitor the course of the treatment, and if necessary can manually input particular parameters such as the duration of irradiation. Suitable monitoring devices (not shown) serve to ensure that the subject is not exposed to electromagnetic radiation S beyond particular safety limit values that are defined ahead of time.

Moreover, here the control device 30 is connected, via an additional interface acting as data input 36, to a bus 90 of a computer network, e.g. an intranet within the organization in which device 10 is being used, or to the Internet. Alternatively, or in addition, a connection to a normal telecommunication line or the like is possible. The intranet can be, for example, a radiological information system RIS in a radiology practice or a hospital or the like.

The device 10 according to the present invention also can receive subject-specific data OD via this additional data interface 36. For example, an RIS can already contain the personal data of the person to be irradiated, such as name, age, height, and weight, so that these data OD can be acquired directly. Likewise, treatment-specific data BD can be acquired (transferred) via such a network. These data OD, BD can then be added to if necessary on location via user interface 40. Preferably, it is also possible via this interface 36 to transfer structure-specific data ID as well as associated resonant frequency patterns RFM from other devices, in particular from outside organizations, and in this way to keep frequency pattern storage unit 33, or the database stored therein, up to date without having to carry out measurements at the device on location for this purpose.

The control device 30 can be, for example, a suitable computer, and the frequency pattern selection unit 32 and the control unit 31 can also at least partly be realized as software. Of course, such a control device 30 also has a multiplicity of additional components (not shown) that are required for the normal function of such a control device 30, such as for example interface cards for connecting the user interface, the bus, and the frequency generator, a power supply, etc. The control device 30 need not necessarily have a one-part construction, as shown; rather, the components of this control device 30 can also be distributed among different devices, e.g. computers. In particular, it is also possible for the frequency pattern storage unit 33 to be composed of a number of storage units, or for areas in larger mass storage units that can be accessed by the control device 30 to be made available for this purpose.

The exemplary embodiment shown in FIG. 1 also has a measurement device 80 with which resonant frequency patterns RFM of a particular biological structure can be determined as needed, if no resonant frequency patterns RFM for a particular biological structure can be found in the database of the frequency pattern storage unit 31 and corresponding data also cannot be obtained via the data input 36, i.e., via the connected network. If, using this measurement device 80, a resonant frequency pattern RFM has been produced for a particular biological structure, for example for a particular new type of virus, this pattern can be provided to the control device 30, and can be stored there in the database situated in the frequency pattern storage unit 33, so that it is available for subsequent radiation sessions. It is likewise possible to give these data to other devices via the connected bus 90, so that these devices can in turn update their frequency pattern storage units.

Figure 2:
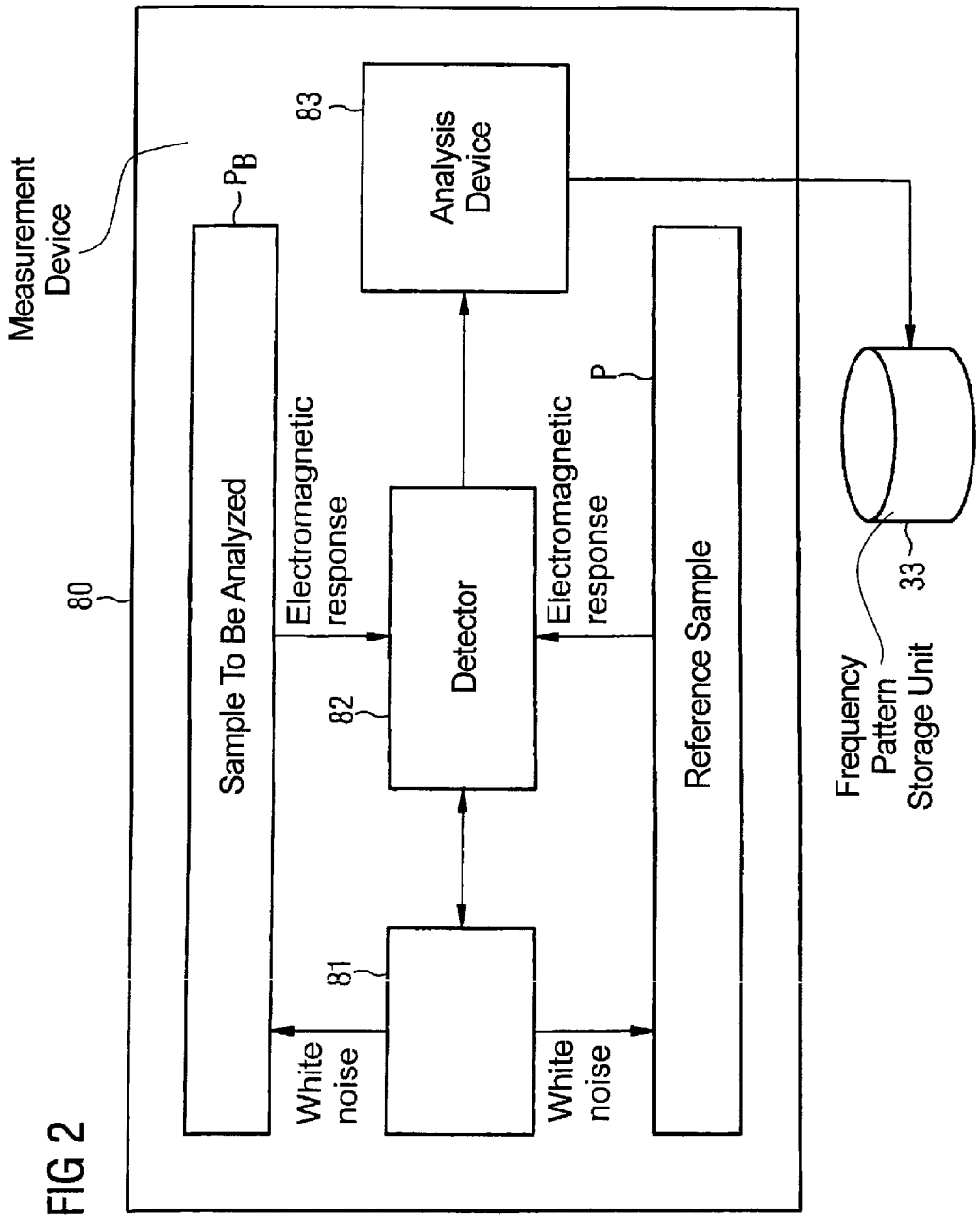
FIG. 2 is a block diagram of a measurement device for determining the resonant frequency pattern of a biological structure.

The functioning of such a measurement device 80 is shown in FIG. 2. This device also has a noise generator 81. The noise generator 81 produces electromagnetic white noise that is radiated onto a sample $P_B$ of a particular medium, for example a nutrient solution, contained in the relevant biological structure, e.g. a microorganism B such as a particular fungus or a bacterium. The white noise is simultaneously also radiated onto another sample P that does not contain the relevant microorganism B.

Methods for isolating a particular microorganism and for preparing suitable samples containing this isolated microorganism, and for preparing corresponding counter-samples, are known to those skilled in the art. Indications thereof are also found in WO 00/15097.

A detector 82 acquires the electromagnetic radiation sent out by samples PB and P in reaction to the white noise. Here, the detector 82 is triggered by the noise generator 81, or vice versa. The electromagnetic responses acquired by detector 82 are supplied to an analysis device 83 that evaluates the respective responses and determines the natural frequencies of the sought microorganism B; i.e., the resonant frequency pattern RFM of this microorganism B. Resonant frequency pattern RFM is then provided to the pattern storage unit 33. The measurement device 80 also can be controlled by the operator via the user interface 40. For example, via the user interface 40 the structure-specific data ID can be inputted for a particular biological structure for which resonant frequency pattern RFM is currently being determined, for example a particular virus or bacteria type, so that a corresponding allocation of resonant frequency pattern RFM to this structure can take place in the measurement device, and thus also in frequency pattern storage device 33.

In an alternative exemplary embodiment (not shown), instead of noise generator 81 a transmitter is used that emits a suitable acoustic resonance signal or signals in the resonance area of the microorganism onto the sample, so that the detector can then acquire the acousto-electromagnetic signature. A more detailed description of the procedure is also found in WO 00/15097.

Figure 3:
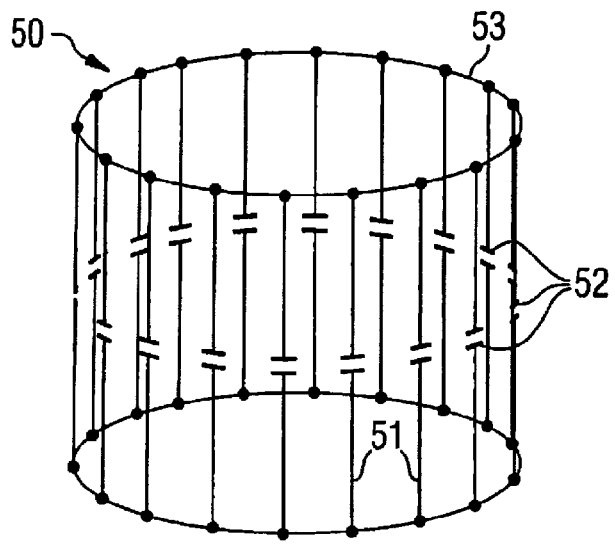
FIG. 3 schematically illustrates a birdcage transmission antenna used in the irradiation device according to FIG. 1.

FIG. 3 schematically shows what is known as a birdcage antenna 50, as is used in the exemplary embodiment according to FIG. 1. This antenna 50 has a cylindrical construction and is composed of longitudinal transverse segments 51 that are connected to one another via circular end rings 53. Capacitors 52 are situated in each of transverse segments 51.

Figure 4:
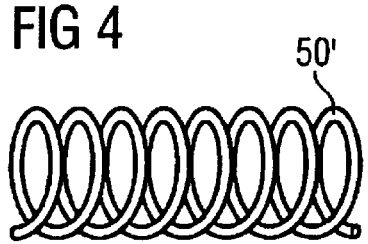
FIG. 4 shows a solenoid coil that can likewise be used as a transmission antenna.
Figure 5:
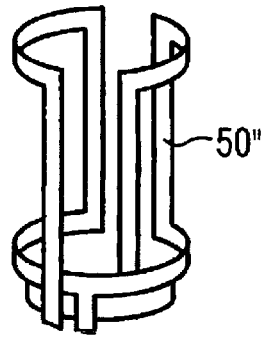
FIG. 5 shows a saddle coil that can likewise be used as a transmission antenna.

FIGS. 3 and 4 show alternative cylindrical antenna 50' and 50"; FIG. 4 shows a simple solenoid coil 50', and FIG. 5 shows what is known as a saddle coil, or also Helmholtz coil, 50". The antennas shown in FIGS. 3 to 5 each have the advantage that a relatively homogenous RF field can be produced within the coils; in particular, the birdcage antenna 50 can have a relatively large construction while nonetheless ensuring a relatively homogenous field propagation in the interior of transmission antenna 50.

The birdcage antenna 50 is particularly well-suited for the creation of a radiation space B in which an entire human body can be situated. In contrast, the saddle coil 50" and the solenoid coil 50' can also be used in particular for local applications, or in order to create a radiation space B for smaller samples, for example inside the measurement device 80, in order to determine a resonant frequency pattern RFM of a particular sample.

FIG. 5 schematically shows a resonant circuit in which for example a solenoid coil 50' can be used as a transmission antenna. By the dimensioning of the capacitors C1, C2, and their relation to resistor R, this resonant circuit can standardly be set to particular resonant frequencies, so that with very little energy a sample can be irradiated with the maximum oscillation amplitude at a defined frequency.

Figure 7:
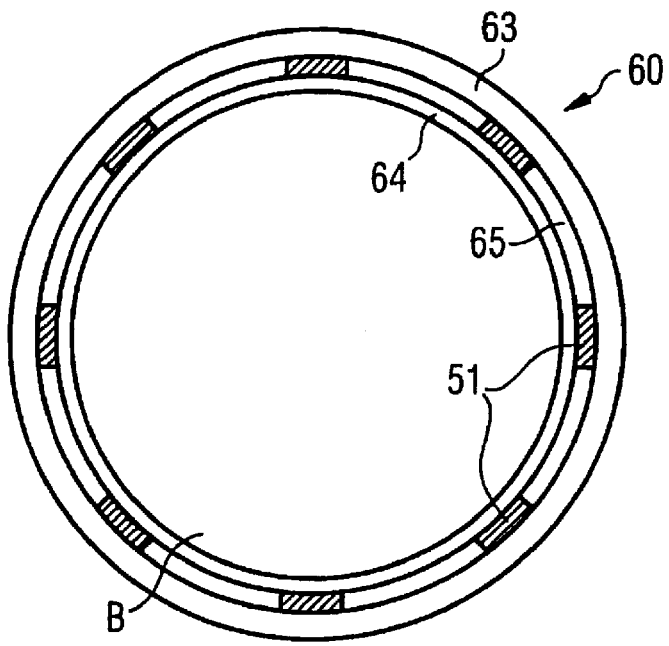
FIG. 7 is a cross-section through an annular housing for an irradiation device according to FIG. 1, having an integrated birdcage antenna.
Figure 8:
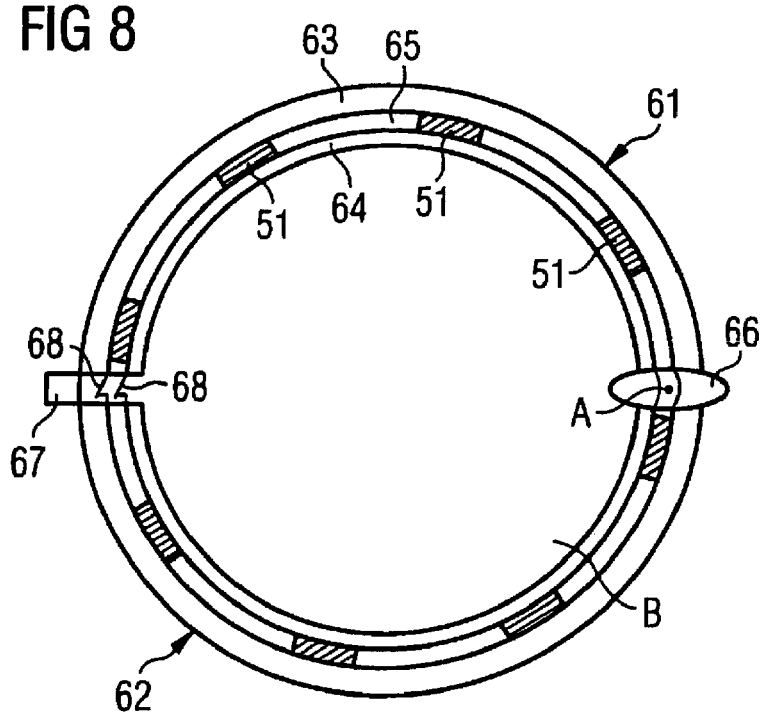
FIG. 8 is a cross-section through a variant of the housing according to FIG. 7, in which the housing can be folded shut along a pivot axis that runs in the longitudinal direction of the housing.

FIGS. 7 and 8, as well as 9A and 9B, each show possible specific embodiments of a housing 60, 60' for the accommodation of a whole-body radiation antenna, for example a birdcage antenna 50.

Figure 6:
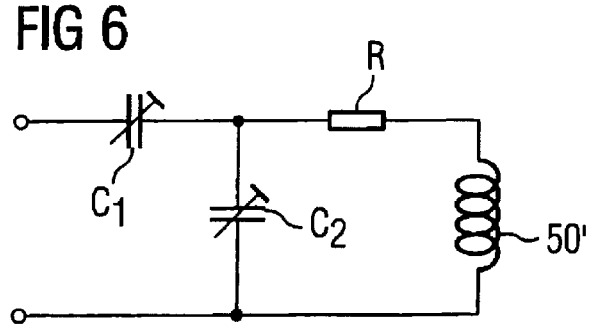
FIG. 6 is a circuit diagram of a resonant circuit for forming a resonant transmission antenna having a solenoid coil according to FIG. 4.

In a specific embodiment according to FIG. 7, the housing is formed by two tubes (or carrier cylinders) 63, 64 situated coaxially to one another. The diameters of these tubes 63, 64 are selected such that there remains between the tubes a gap 65 in which the antenna structure is held. In FIG. 6, transverse segments 51 with capacitors 52 are shown schematically in this intermediate space 65. The tubes 63, 64 preferably are made of a transparent material, so that a person situated inside radiation space B can look out through housing 60 and through the antenna structure. The antenna structure is fashioned and situated such that the field homogeneity is as large as possible over the entire radiation space B, while the grid-like antenna structure still ensures overall transparency.

Figure 9A:
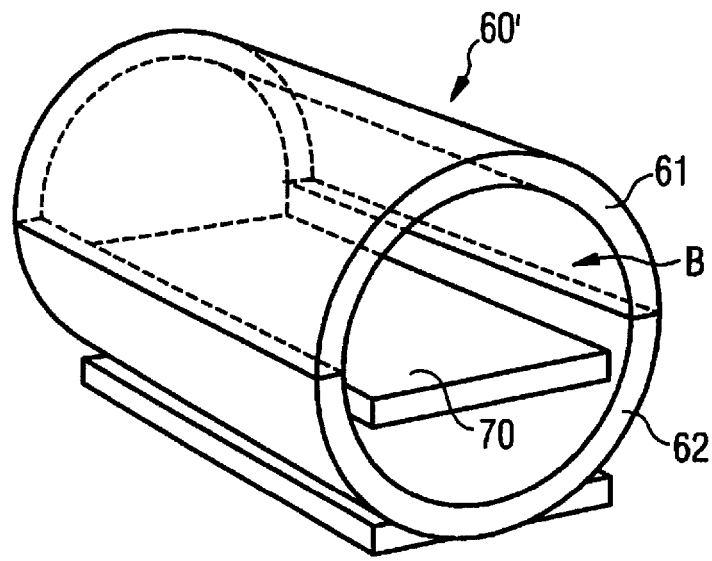
FIG. 9A is a perspective schematic representation of the housing according to FIG. 8, having a transparent housing cover.
Figure 9B:
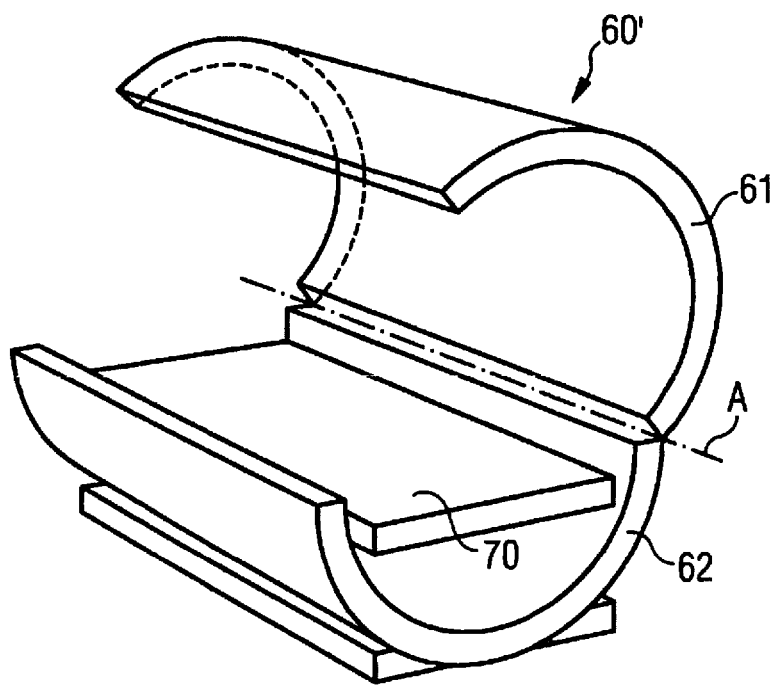
FIG. 9B shows the housing according to FIG. 9A, but with the housing cover opened.

FIGS. 8, 9A, and 9B show another variant of a housing 60', formed by a housing cover 61 and a housing base 62 with a treatment platform 70 situated therein. The housing cover 61 is fastened on one side so as to be able to be pivoted upward about a pivot axis A on the housing base 62 that runs in the longitudinal direction of the housing 60', so that the person to be irradiated can lie down comfortably in the housing 60' on the platform 70, and can subsequently fold down the housing cover 61.

FIG. 8 shows a schematic cross-section through this housing 60'. The basic design is the same as in the exemplary embodiment according to FIG. 7, but here the housing 60' is divided along a horizontal plane into an upper part, the housing cover 61, and a lower part, the housing base 62. On a longitudinal side, the housing cover 61 and the housing base 62 are connected to one another by a hinge 66. On the other side, between the housing cover 61 and the housing base 62, there are situated a stop 67 and contacts 68 in order to connect the antenna structure in the housing cover 61 to the antenna structure in the housing base 62 in the closed state. The stop 67 simultaneously acts as a handle for pivoting the housing cover 61 upwardly. Corresponding contacts also run through the hinge 66, so that when the housing 60' is closed, antenna 50 produces the same field as in the exemplary embodiment according to FIG. 7.

In the exemplary embodiment shown in FIG. 8, it is sufficient if (as is shown in FIGS. 9A and 9B) inner and outer cylinder walls 63, 64 of the housing cover 61 are made of transparent material. The walls of the housing base 62 also can be made of non-transparent material.

Using the inventive device, arbitrary viral or bacterial infections, fungal infections, etc., of persons or of animals can be therapeutically treated in a manner that treats the patient gently, i.e., is not invasive. The realization of the device as a whole-body treatment ensures that, in the case of an infection, as long as all the body regions are treated the viruses, bacteria, or fungi in the body can be completely destroyed. Through the use according to the present invention of a frequency pattern storage unit in which defined resonant frequency patterns allocated to various biological structures are stored, a treatment can be begun as soon as a particular virus, bacteria, or fungus is identified and the resonant frequency pattern has been determined; this can take place without great expense, because only the viruses or bacteria, fungi, or the like are destroyed in a targeted fashion, and no harmful effect is exerted on other biological structures in the organism. In addition, the device can be successfully used for other treatments in which a targeted influencing of defined biological structures is desirable, such as diseases involving tumors, leukemia, etc. The precondition for this is merely that the precise resonant frequency patterns of these structures be known. The device is relatively economical to construct.

Although modifications and changes may be suggested by those skilled in the art, it is the intention of the inventor to embody within the patent warranted hereon all changes and modifications as reasonably and properly come within the scope of his contribution to the art.

I claim as my invention:

1. An irradiation device for irradiating a living organism with electromagnetic radiation to influence a biological structure within the organism, said irradiation device comprising:

an interface that acquires structure-specific data that define a biological target structure in an organism to be influenced by irradiation with electromagnetic radiation;

a frequency pattern storage unit in which a number of defined resonant frequency patterns are stored, said defined resonant frequency patterns being respectively allocated to different biological structures, each defined resonant frequency pattern being defined as a frequency pattern of electromagnetic radiation representing an acoustic-electromagnetic signature of the allocated biological target structure for targeted setting of the allocated biological structure into a state of resonance;

a frequency pattern selection unit connected to said interface that selects, dependent on the structure-specific data acquired by said interface, one of the defined resonant frequency patterns stored in said frequency pattern storage unit;

a frequency generator having a frequency synthesizer that emits an electrical signal to produce electromagnetic radiation having a frequency pattern;

a transmission antenna supplied with said electrical signal that radiates said electromagnetic radiation having said frequency pattern into a radiation volume in which said organism is disposed; and a control unit connected to said frequency generator and to said frequency pattern selection unit, said control unit controlling said frequency generator, dependent on the selected, defined resonant frequency pattern, to emit an electrical signal that causes said transmission antenna to radiate electromagnetic radiation into said radiation volume having the selected, defined resonant frequency pattern, and having an intensity and duration defined by said control unit.

2. A device as claimed in claim 1 comprising an interface for acquiring therapeutic data selected from the group consisting of organism-specific data and treatment-specific data, and wherein said control unit is supplied with said therapeutic data and controls said frequency generator to cause said transmission antenna to emit said electromagnetic radiation with said defined frequency pattern, said defined intensity and said defined duration being set by said control unit dependent on said therapeutic data, as a therapeutic dose of said electromagnetic radiation.

3. A device as claimed in claim 1 wherein said transmission antenna radiates said electromagnetic radiation into a radiation volume having a size adapted to encompass at least a portion of an adult subject as said organism.

4. A device as claimed in claim 1 wherein said transmission antenna comprises a resonant circuit.

5. A device as claimed in claim 1 wherein said transmission antenna comprises a conductor arrangement that surrounds said radiation volume, said conductor arrangement being configured as an arrangement selected from the group consisting of a solenoid coil, a Helmholtz coil, and a birdcage antenna.

6. A device as claimed in claim 1 wherein said resonant frequency pattern storage unit stores a number of said resonant frequency patterns for respective viruses and bacteria.

7. A device as claimed in claim 1 comprising a housing enclosing said radiation volume and wherein said transmission antenna is integrated in said housing.

8. A device as claimed in claim 7 wherein at least a portion of said housing is formed of transparent material.

9. A device as claimed in claim 7 wherein said housing has a tube-shaped interior, with said radiation volume being disposed in said tube-shaped interior.

10. A device as claimed in claim 7 wherein said housing is divided into two housing parts by a plane disposed in a longitudinal direction of said housing, said housing parts comprising a housing base and a housing cover that is connected to said housing base to allow said housing cover to the opened and closed relative to said housing base.

11. A device as claimed in claim 1 comprising a measurement device that determines the resonant frequency pattern for the biological target structure in the organism to be irradiated.

12. A device as claimed in claim 11 wherein said measurement device comprises a noise generator that emits electromagnetic white noise in a predetermined frequency range into a sample corresponding to biological target structure, a detector that acquires electromagnetic radiation emitted by said sample in response to said white noise, and an analysis device that determines said residence frequency pattern from the electromagnetic radiation detected by said detector.

13. A device as claimed in claim 11 wherein said measurement device comprises an acoustic generator that emits sound waves in a predetermined frequency range into a sample corresponding to said biological target structure, a detector that acquires electromagnetic radiation emitted by said sample in response to said sound waves, and an analysis device that determines said resonant frequency pattern from the electromagnetic radiation detected by said detector.

14. A device as claimed in claim 11 wherein said measurement device is connected to said frequency pattern storage unit, said measurement device transferring the resonant frequency pattern for the biological target structure, determined by said measurement device, to said frequency pattern storage unit for storage therein, and wherein said frequency pattern storage unit stores said resonant frequency pattern of said biological target structure with an identification of said biological target structure.

15. A control device for an irradiation device for irradiating a living organism with electromagnetic radiation to influence a biological structure within the organism, said irradiation device comprising a frequency generator having a frequency synthesizer that emits an electrical signal to produce electromagnetic radiation having a frequency pattern, and a transmission antenna supplied with said electrical signal that radiates said electromagnetic radiation having said frequency pattern into a radiation volume in which said organism is disposed, said control device comprising:

an interface that acquires structure-specific data that define a biological target structure in said organism to be influenced by said electromagnetic radiation;

a frequency pattern storage unit in which a number of defined resonant frequency patterns are stored, said defined resonant frequency patterns being respectively allocated to different biological structures, each defined resonant frequency pattern being defined as a frequency pattern of electromagnetic radiation representing an acoustic-electromagnetic signature of the allocated biological target structure for targeted setting of the allocated biological structure into a state of resonance;

a frequency pattern selection unit that selects, dependent on the acquired structured-specific data, one of the defined resonant frequency patterns stored in said frequency pattern storage unit; and a control unit connected to said frequency generator and to said frequency pattern selection unit, said control unit controlling said frequency generator, dependent on the selected, defined resonant frequency pattern, to emit an electrical signal that causes said transmitter to radiate electromagnetic radiation into said radiation volume having the selected, defined resonant frequency pattern and having an intensity and duration defined by said control unit.

\* \* \* \* \*